(12) United States Patent
Parnis et al.

(10) Patent No.: US 7,840,280 B2
(45) Date of Patent: Nov. 23, 2010

(54) CRANIAL NERVE STIMULATION TO TREAT A VOCAL CORD DISORDER

(75) Inventors: Steven M. Parnis, Pearland, TX (US); Steven E. Maschino, Seabrook, TX (US); Albert W. Guzman, League City, TX (US)

(73) Assignee: Cyberonics, Inc., Houston, TX (US)

( * ) Notice: Subject to any disclaimer, the term of this patent is extended or adjusted under 35 U.S.C. 154(b) by 651 days.

(21) Appl. No.: 11/191,121

(22) Filed: Jul. 27, 2005

(65) Prior Publication Data

US 2007/0027482 A1 Feb. 1, 2007

(51) Int. Cl.
*A61N 1/00* (2006.01)

(52) U.S. Cl. ...................................... 607/116

(58) Field of Classification Search ............ 607/2, 607/116, 136, 41; 623/9
See application file for complete search history.

(56) References Cited

U.S. PATENT DOCUMENTS

| | | | |
|---|---|---|---|
| 4,431,000 A | 2/1984 | Butler et al. | |
| 4,503,863 A | 3/1985 | Katims | |
| 4,541,432 A | 9/1985 | Molina-Negro et al. | |
| 4,556,064 A | 12/1985 | Pomeranz et al. | |
| 4,573,481 A | 3/1986 | Bullara | |
| 4,702,254 A | 10/1987 | Zabara | |
| 4,865,048 A | 9/1989 | Eckerson | |
| 4,867,164 A | 9/1989 | Zabara | |
| 4,977,895 A | 12/1990 | Tannenbaum | |
| 4,979,511 A | 12/1990 | Terry, Jr. | |
| 5,025,807 A | 6/1991 | Zabara | |
| 5,154,172 A | 10/1992 | Terry, Jr. et al. | |
| 5,188,104 A | 2/1993 | Wernicke et al. | |

(Continued)

FOREIGN PATENT DOCUMENTS

EP 1070518 1/2001

(Continued)

OTHER PUBLICATIONS

Bachman, D.S, et al., "Effects of Vagal Volleys and Serotonin on Units of Cingulate Cortex in Monkeys," Brain Research, 130, (1977), pp. 253-269.

(Continued)

*Primary Examiner*—George Manuel
(74) *Attorney, Agent, or Firm*—Williams, Morgan & Amerson, P.C.; Timothy L. Scott

(57) ABSTRACT

Disclosed is a method of treating a patient having a vocal cord disorder, comprising coupling at least one electrode to at least one cranial nerve of the patient, wherein the cranial nerve is selected from the group consisting of a vagus nerve, a trigeminal nerve, and a glossopharyngeal nerve, and applying an electrical signal to the cranial nerve using the electrode to treat the vocal cord disorder. The electrode may be coupled to a branch of the vagus nerve selected from the group consisting of a recurrent laryngeal nerve, the external branch of a superior laryngeal nerve, the internal branch of a superior laryngeal nerve, and a pharyngeal plexus. Also disclosed is a computer readable program storage device encoded with instructions that, when executed by a computer, perform the method, and a medical device and a vocal cord disorder treatment system that may be used in performance of the method.

18 Claims, 7 Drawing Sheets

U.S. PATENT DOCUMENTS

| | | |
|---|---|---|
| 5,205,285 A | 4/1993 | Baker, Jr. |
| 5,215,086 A | 6/1993 | Terry, Jr. et al. |
| 5,231,988 A | 8/1993 | Wernicke et al. |
| 5,243,980 A | 9/1993 | Mehra |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker et al. |
| 5,306,298 A * | 4/1994 | Godley et al. .................. 623/9 |
| 5,330,515 A | 7/1994 | Rutecki et al. |
| 5,335,657 A | 8/1994 | Terry, Jr. et al. |
| 5,458,625 A | 10/1995 | Kendall |
| 5,514,175 A * | 5/1996 | Kim et al. .................. 607/136 |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,769,778 A | 6/1998 | Abrams et al. |
| 5,792,210 A | 8/1998 | Wamubu et al. |
| 5,792,212 A | 8/1998 | Weijand |
| 5,814,092 A | 9/1998 | King |
| 5,830,434 A | 11/1998 | Taylor et al. |
| 5,836,994 A | 11/1998 | Bourgeois |
| 5,861,014 A | 1/1999 | Familoni |
| 5,861,022 A | 1/1999 | Hipskind |
| 5,916,239 A | 6/1999 | Geddes et al. |
| 5,919,216 A | 7/1999 | Houben et al. |
| 5,928,272 A | 7/1999 | Adkins et al. |
| 6,002,966 A | 12/1999 | Loeb et al. |
| 6,006,134 A | 12/1999 | Hill et al. |
| 6,044,846 A | 4/2000 | Edwards |
| 6,073,048 A | 6/2000 | Kieval et al. |
| 6,092,528 A | 7/2000 | Edwards |
| 6,097,984 A | 8/2000 | Douglas |
| 6,104,956 A | 8/2000 | Naritoku et al. |
| 6,109,269 A | 8/2000 | Rise et al. |
| 6,132,361 A | 10/2000 | Epstein et al. |
| 6,152,953 A | 11/2000 | Hipskind |
| 6,188,929 B1 | 2/2001 | Giordano |
| 6,219,580 B1 | 4/2001 | Faltys et al. |
| 6,233,488 B1 | 5/2001 | Hess |
| 6,259,951 B1 | 7/2001 | Kuzma et al. |
| 6,295,472 B1 | 9/2001 | Rubenstein et al. |
| 6,304,787 B1 | 10/2001 | Kuzma et al. |
| 6,339,725 B1 | 1/2002 | Naritoku et al. |
| 6,341,236 B1 | 1/2002 | Osorio et al. |
| 6,374,140 B1 | 4/2002 | Rise |
| 6,381,499 B1 | 4/2002 | Taylor et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,463,328 B1 | 10/2002 | John |
| 6,473,644 B1 | 10/2002 | Terry, Jr. et al. |
| 6,505,074 B2 | 1/2003 | Boveja et al. |
| 6,532,388 B1 | 3/2003 | Hill et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,609,025 B2 | 8/2003 | Barrett et al. |
| 6,610,713 B2 | 8/2003 | Tracey |
| 6,622,041 B2 | 9/2003 | Terry, Jr. et al. |
| 6,647,296 B2 | 11/2003 | Fischell et al. |
| 6,721,603 B2 | 4/2004 | Zabara et al. |
| 6,885,888 B2 | 4/2005 | Rezai |
| 6,908,487 B2 | 6/2005 | Cigaina |
| 7,069,082 B2 * | 6/2006 | Lindenthaler ................ 607/41 |
| 7,299,091 B2 * | 11/2007 | Barrett et al. .................. 607/2 |
| 2002/0116030 A1 | 8/2002 | Rezai |
| 2002/0151939 A1 | 10/2002 | Rezai |
| 2003/0055457 A1 | 3/2003 | MacDonald |
| 2003/0208212 A1 | 11/2003 | Cigaina |
| 2003/0236558 A1 | 12/2003 | Whitehurst et al. |
| 2004/0015205 A1 | 1/2004 | Whitehurst et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0210270 A1 | 10/2004 | Erickson |
| 2004/0249416 A1 | 12/2004 | Yun et al. |
| 2005/0010262 A1 | 1/2005 | Rezai et al. |
| 2005/0021092 A1 | 1/2005 | Yun et al. |
| 2005/0038484 A1 | 2/2005 | Knudson et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065575 A1 | 3/2005 | Dobak |
| 2005/0075681 A1 | 4/2005 | Rezai et al. |
| 2005/0075701 A1 | 4/2005 | Shafer |
| 2005/0131485 A1 | 6/2005 | Knudson et al. |
| 2005/0131486 A1 | 6/2005 | Boveja et al. |
| 2005/0131506 A1 | 6/2005 | Rezai et al. |
| 2005/0192644 A1 | 9/2005 | Boveja et al. |
| 2006/0020292 A1 | 1/2006 | Goetz et al. |

FOREIGN PATENT DOCUMENTS

| | | |
|---|---|---|
| EP | 1145736 | 10/2001 |
| GB | 2079610 | 1/1982 |
| WO | 9302744 | 2/1993 |
| WO | 2004036377 A2 | 4/2004 |
| WO | 2005007120 A2 | 1/2005 |
| WO | 2005028026 A1 | 3/2005 |

OTHER PUBLICATIONS

Bohning, D.E. et al., "Feasibility of Vagus Nerve Stimulation-Synchronized Blood Oxygenation Level-Dependent Functional MRI," Investigative Radiology, vol. 36, No. 8, (Aug. 2001), pp. 470-479.

Clark, K.B., et al., "Posttraining Electrical Stimulation of Vagal Afferents With Concomitant Vagal Efferetn Inactivation Enhances Memory Storage Processes In The Rat," Neurobiology of Learning and Memory 70, Article No. NL983863, (1998) pp. 364-373.

Degiorgio, Christopher M. et al., "Vagus Nerve Stimulation: Analysis of Device Parameters in 154 Patients During The Long-Term XE5 Study," Epilepsia, vol. 42, No. 8, 2001, pp. 1017-1020.

Dodrill, Carl B. et al., "Effects of Vagal Nerve Stimulation on Cognition And Quality of Life in Epilepsy," Epilepsy & Behavior, vol. 2, 2001, pp. 46-53.

George, Mark S. et al., "Open Trial of VNS Therapy in Severe Anxiety Disorders," 156th American Psychiatric Association Annual Meeting, May 17-22, 2003, San Francisco, California, 1 page.

Hallowitz, R.A., et al., "Effects of Vagal Volleys on Units of Intralaminar and Juxtalaminar Thalamic Nuclei in Monkeys," Brain Research, 130, (1977), pp. 271-286.

Henry, Thomas R. et al., "Brain Blood Flow Alterations Induced BY Therapeutic Vagus Nerve Stimulation in Partial Epilepsy: I. Acute Effects At High And Low Levels of Stimulation," Epilepsia, vol. 39, No. 9, 1998, pp. 983-990.

Henry, Thomas R., "Therapeutic Mechanisms of Vagus Nerve Stimulation," Neurology, vol. 59, Suppl. 4, Sep. 2002, pp. S3-S14.

Kling, Michael A., et al., "Effects of Short-Term Vagus Nerve Stimulation (VNS) on FOS Expression in Rat Brain Nuclei," 58th Annual Scientific Convention of The Society of Biological Psychiatry, May 15-17, 2003, San Francisco, California, 1 page.

Klapper, Jack A. et al., "VNS Therapy Shows Potential Benefit in Patients With Migraine and Chronic Daily Headache After 3 to 6 Months of Treatment (Preliminary Results)," 45th Annual Scientific Meeting of the American Headache Society, Jun. 19-22, 2003, Chicago, Illinois, 1 page.

Koo, Betty, "EEG Changes With Vagus Nerve Stimulation," Journal of Clinical Neurophysiology, vol. 18, No. 5, (Sep. 2001), pp. 434-441.

Lockard, J.S., et al., "Feasibility and Safety of Vagal Stimulation in Monkey Model," Epilepsia, 31, (Suppl.2), (1990), pp. S20-S26.

Schacter, Steven C., et al., "Vagus Nerve Stimulation," Epilepsia, vol. 39, No. 7, 1998, pp. 677-686.

Tatum, IV, W.O. et al., "Ventricular Asystole During Vagus Nerve Stimulation For Epilepsy in Humans," Neurology, vol. 52, 1999, pp. 1267-1269.

Tatum, IV, W.O. et al., "Vagus Nerve Stimulation And Drug Reduction," Neurology, vol. 56, No. 4, Feb. 2001, pp. 561-563.

Terry, R.S., et al., "The Implantable Neurocybernetic Prosthesis System," Pacing and Clinical Electrophysiology, vol. 14, No. 1, (Jan. 1991), pp. 86-93.

Tubbs, R. Shane et al., "Left-Sided Vagus Nerve Stimulation Decreases Intracranial Pressure Without Resultant Bradycardia in The Pig: A Potential Therapeutic Modality for Humans," Child's Nervous System, Springer-Verlag, 2004, pp. 1-6.

Valdes-Cruz, Alejandro et al., "Chronic Stimulation of The Cat Vagus Nerve Effect on Sleep And Behavior," Progress in Neuro-Psychopharmacology & Biological Psychiatry, No. 26, 2002, pp. 113-118.

Vonck, K., et al., "The Mechanism of Action of Vagus Nerve Stimulation for Refractory Epilepsy," Journal of Neurophysiology, vol. 18, No. 5, (Sep. 2001), pp. 394-401.

Ward, Hebert et al., "Treatment-Refractory Obsessive-Compulsive Disorder: Potential Benefit of VNS Therapy," 23rd Annual Conference of The Anxiety Disorders Association of America, Mar. 27-30, 2003, Toronto, Canada, 1 page.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., et al., "Inhibition of Experimental Seizures in Canines by Repetitive Vagal Stimulation," Epilepsia, 33(6), (1992), pp. 1005-1012.

* cited by examiner

CRANIAL NERVE STIMULATION TO TREAT A VOCAL CORD DISORDER

BACKGROUND OF THE INVENTION

The present invention relates generally to methods and apparatus for treating disorders by cranial nerve stimulation. More particularly, it concerns methods and apparatus for treating vocal cord disorders by vagus nerve stimulation, particularly stimulation of one or more branches of the vagus nerve enervating the vocal cords.

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Jacob Zabara, which is hereby incorporated in its entirety herein by reference in this specification. Electrical stimulation of the vagus nerve (hereinafter referred to as vagus nerve stimulation therapy or VNS) may be provided by implanting an electrical device underneath the skin of a patient and performing an electrical stimulation process, which may optionally include a sensor to detect a symptom of a disorder or condition of interest, which may then be used to trigger the electrical stimulation. Alternatively, the system may operate without a detection system once the patient has been diagnosed with a disorder, and may periodically apply a series of electrical pulses to the vagus (or other cranial) nerve intermittently throughout the day, or over another predetermined time interval.

A nerve bundle to which neurostimulation therapy is applied may comprise up to 100,000 or more individual nerve fibers of different types, including larger diameter A and B fibers which comprise a myelin sheath and C fibers which have a much smaller diameter and are unmyelinated. Different types of nerve fibers respond differently to different types of stimulation signals. These different responses among nerve fiber types reflect, among other things, their different sizes, conduction velocities, stimulation thresholds, and myelination status (i.e., myelinated or unmyelinated). Therefore, the patient's body may respond differently depending on which type(s) of nerve fibers are the target of the stimulation therapy. In general, the larger, myelinated A and B fibers have a lower stimulation threshold than the unmyelinated, smaller C fibers.

The vocal cords are a pair of bands of elastic muscle located side-by-side in the larynx (voicebox), between the trachea (windpipe) and the upper respiratory region (nasal passages, mouth, sinuses, and throat). When the vocal cords are partially or fully closed and air is exhaled from the lungs, the exhaled air causes the vocal cords to vibrate, generating sounds of various pitches and intensities. If the ability to open and close one or both vocal cords is impaired, the quality of a person's voice is diminished. Paralysis of one or both vocal cords may lead to a significant impairment or complete loss of the ability to speak.

Another potential source of diminished voice quality may be effects of a mechanical or electrical apparatus or attachment thereto located in proximity to a person's larynx and performing repeated actions with a certain frequency (e.g., about 50 Hz). At such a frequency, the vocal cords may resonate contrary to the volition of the person and diminish voice quality.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
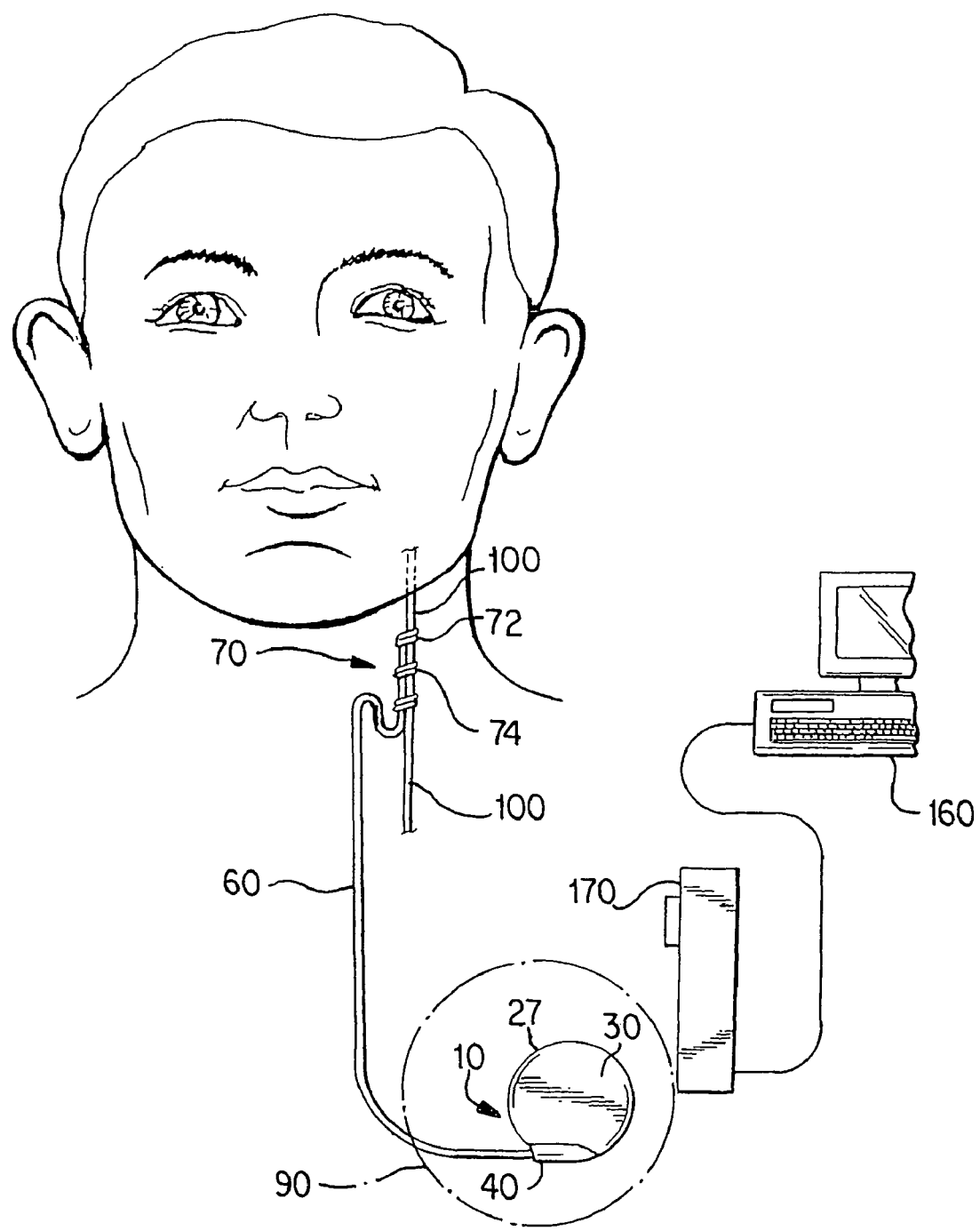
FIG. 1 illustrates a neurostimulator system for stimulating the vagus nerve 100 of a patient, in accordance with one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Certain terms are used throughout the following description and claims to refer to particular system components. As one skilled in the art will appreciate, components may be referred to by different names. This document does not intend to distinguish between components that differ in name but not function. In the following discussion and in the claims, the terms "including" and "comprising" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated. All patents and patent applications specifically referred to herein are hereby incorporated by reference in the present application.

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiment of the present invention provide for the treatment of vocal cord disorders by stimulation of cranial nerves. The vocal cord disorder may comprise vocal cord paralysis and/or vocal cord trauma.

Cranial nerve stimulation has been used successfully to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict. Accordingly, cranial nerve stimulation, and particularly vagus nerve stimulation, has not heretofore been deemed appropriate for use in treating vocal cord disorders.

A number of cranial nerves innervate the vicinity of the larynx. The trigeminal nerve (fifth cranial nerve), glossopharyngeal nerve (ninth cranial nerve), and the vagus nerve (tenth cranial nerve) provide branches to the pharyngeal plexus, which innervates muscles and mucosa of the pharynx and many of the muscles of the soft palate. The superior laryngeal nerve is a branch of the vagus nerve, which itself branches to an external branch and an internal branch. The external branch of the superior laryngeal nerve innervates the sternohyoid, the cricothyroid, and part of the constrictor pharynges inferior muscle. The internal branch of the superior laryngeal nerve innervates the glands of the epiglottis, the base of the tongue, the aryepiglottic fold, and the larynx superior to the vocal folds. The recurrent laryngeal nerve is another branch of the vagus nerve, and it innervates the muscles of the larynx other than the cricothyroid.

Disclosed herein is a method for treating a vocal cord disorder using stimulation of the vagus nerve (tenth cranial nerve). One or more other cranial nerves may be stimulated in addition to the vagus nerve, including the trigeminal nerve (fifth cranial nerve), the vestibulocochlear nerve (eighth cranial nerve), and the glossopharyngeal nerve (ninth cranial nerve), among others. Stimulation of the glossopharyngeal nerve may be used in treating salivation disorders. A generally suitable form of neurostimulator for use in the method and apparatus of the present invention is disclosed, for example, in U.S. Pat. No. 5,154,172, assigned to the same assignee as the present application. The neurostimulator may be referred to as a NeuroCybernetic Prosthesis (NCP®, Cyberonics, Inc., Houston, Tex., the assignee of the present application). Certain parameters of the electrical stimuli generated by the neurostimulator are programmable, such as be means of an external programmer in a manner conventional for implantable electrical medical devices.

In one embodiment, the present invention relates to a method of treating a patient having a vocal cord disorder, including coupling at least one electrode to at least one cranial nerve of the patient, wherein the cranial nerve is selected from the group consisting of a vagus nerve, a trigeminal nerve, and a glossopharyngeal nerve, and applying an electrical signal to the at least one cranial nerve using the electrode to treat the vocal cord disorder. The vocal cord disorder may comprise paralysis and/or vocal cord trauma.

As used herein, the term "at least one cranial nerve" refers to the group consisting of a left cranial nerve and a right cranial nerve. The term "cranial nerve" refers to any portion of the main trunk or any branch of a cranial nerve or plexus including cranial nerve fibers. In one embodiment, coupling the at least one electrode includes coupling the at least one electrode to a branch of the vagus nerve of the patient selected from the group consisting of a recurrent laryngeal nerve, the external branch of a superior laryngeal nerve, the internal branch of a superior laryngeal nerve, and a pharyngeal plexus.

Methods of the present invention may further comprise generating a physiological response to the electrical signal that is selected from the group consisting of an afferent action potential, an efferent action potential, an afferent hyperpolarization, and an efferent hyperpolarization. In one embodiment, applying the electrical signal to the cranial nerve may include generating an efferent action potential.

In one embodiment, the method may further include providing a programmable electrical signal generator, coupling the signal generator to the at least one electrode, generating an electrical signal with the electrical signal generator, and applying the electrical signal to the electrode.

In one embodiment, the method may further include programming the electrical signal generator to define the electrical signal by at least one parameter selected from the group consisting of a current magnitude, a pulse frequency, a pulse width, an on-time and an off-time, wherein the at least one parameter is selected to treat the vocal cord disorder.

In one embodiment, the method may further include detecting a symptom of the vocal cord disorder, wherein applying the electrical signal to the cranial nerve is initiated in response to the detecting the symptom. In a further embodiment, the detecting the symptom may be performed by the patient. This may involve a subjective observation by the patient that he is experiencing a symptom of the vocal cord disorder. Alternatively or in addition, the symptom may be detected by performing a voice test on the patient, by using a voice sensor, or by visualizing brain function by an EKG, MRI, or PET scan to observe any cortical response typical of the vocal cord disorder.

The method may be performed under a single treatment regimen or under multiple treatment regimens. "Treatment regimen" herein refers to a parameter of the electrical signal, a duration for applying the signal, or a duty cycle of the signal, among others. In one embodiment, applying the electrical signal to the cranial nerve is performed during a first treatment period, and the method further includes applying a second electrical signal to the cranial nerve using the at least one electrode during a second treatment period to treat the vocal cord disorder. In a further embodiment, the method may further include detecting a symptom of the vocal cord disorder, wherein the second treatment period is initiated in response to detecting a symptom of the vocal cord disorder. For example, a patient suffering a vocal cord disorder typically presenting with a set of chronic symptoms, but who also periodically suffers acute episodes of the vocal cord disorder presenting a set of symptoms that is different from or more intense than one or more chronic symptoms, may benefit by receiving a first electrical signal during a first, chronic treatment period and a second electrical signal during a second, acute treatment period. Three or more treatment periods may be used, if deemed desirable by a medical practitioner.

In one particular embodiment, the present invention relates to a method of treating a patient having a vocal cord disorder, including coupling at least one electrode to at least one cranial nerve of the patient selected from the group consisting of a vagus nerve, a trigeminal nerve, and a glossopharyngeal nerve, providing an electrical signal generator, coupling the signal generator to the at least one electrode, generating an electrical signal with the electrical signal generator, and applying the electrical signal to the electrode to treat the vocal cord disorder. The invention may further comprise detecting a symptom of the vocal cord disorder, wherein the step of applying the electrical signal to the electrode is initiated in response to detecting the symptom.

In another embodiment, coupling at least one electrode to at least one cranial nerve includes coupling at least one electrode to a branch of the vagus nerve of the patient selected from the group consisting of a recurrent laryngeal nerve, the external branch of a superior laryngeal nerve, the internal branch of a superior laryngeal nerve, and a pharyngeal plexus.

In a further embodiment, the invention comprises a method of treating a patient having a vocal cord disorder by coupling at least one electrode to at least one branch of a vagus nerve of the patient selected from the group consisting of a recurrent laryngeal nerve, the external branch of a superior laryngeal nerve, the internal branch of a superior laryngeal nerve, and a pharyngeal plexus, and applying an electrical signal to the at least one branch of a vagus nerve using the electrode. The invention may further comprise providing a programmable electrical signal generator, coupling the signal generator to the at least one electrode, generating an electrical signal with the electrical signal generator, and applying the electrical signal to the at least one branch of a vagus nerve may comprise applying the electrical signal to the at least one electrode. The invention may further comprise programming the electrical signal generator to define the electrical signal by a plurality of parameters selected from the group consisting of a current magnitude, a pulse frequency, a pulse width, an on-time and an off-time. In another embodiment, the step of applying an electrical signal to the at least one branch of a vagus nerve includes applying the signal during a first treatment period, and the method further comprises applying a second electrical signal to the at least one branch of a vagus nerve during a second treatment period. The first treatment period may comprise a period ranging from one hour to six months, and the second treatment period may comprise a period ranging from one month to 10 years. In another embodiment, the at least one electrode comprises an electrode selected from the group consisting of a spiral electrode and a paddle electrode.

In one embodiment, the present invention relates to a computer readable program storage device encoded with instructions that, when executed by a computer, perform a method including generating an electrical signal and providing the electrical signal to a cranial nerve of a patient using an electrode to treat a vocal cord disorder, wherein the cranial nerve is selected from the group consisting of a vagus nerve, a trigeminal nerve, and a glossopharyngeal nerve.

In one embodiment wherein the computer readable program storage device is encoded with instructions that, when executed by a computer, performs the method, the electrical signal may be a controlled current electrical signal.

In one embodiment wherein the computer readable program storage device encoded with instructions that, when executed by a computer, performs the method, the method may further include programming an electrical signal generator to define the electrical signal by at least one parameter selected from the group consisting of a current magnitude, a pulse frequency, and a pulse width, wherein the parameter is selected to treat the vocal cord disorder.

In one embodiment wherein the computer readable program storage device is encoded with instructions that, when executed by a computer, performs the method, the method may further include detecting a symptom of the vocal cord disorder, wherein the providing the electrical signal is initiated in response to the detecting the symptom.

In one embodiment, the present invention relates to a vocal cord disorder treatment system, including at least one electrode coupled to at least one cranial nerve of a patient, wherein the cranial nerve is selected from the group consisting of a vagus nerve, a trigeminal nerve, and a glossopharyngeal nerve, and an implantable device operatively coupled to the electrode and including an electrical signal generator capable of applying an electrical signal to the cranial nerve using the electrode to treat the vocal cord disorder.

The at least one electrode and its coupling to the at least one cranial nerve may be as described above.

The electrical signal generator may be capable of triggering an efferent action potential. The electrical signal generator may be a programmable electrical signal generator. The electrical signal generator may be capable of defining the electrical signal by at least one parameter selected from the group consisting of a current magnitude, a pulse frequency, and a pulse width, wherein the at least one parameter is selected to treat the vocal cord disorder. The vocal cord disorder treatment system may further include a detection communicator capable of delivering, directly or indirectly, at least one signal to the electrical signal generator, and wherein the electrical signal generator is capable of applying the electrical signal on receipt of the at least one signal from the detection communicator. In a further embodiment, the at least one signal communicated by the detection communicator may be generated by the patient.

Specific embodiments of the present invention will now be discussed with reference to the various figures.

FIG. 1 illustrates a neurostimulator system for stimulating the vagus nerve 100 of a patient, in accordance with one embodiment of the present invention. Electrical signal generator 10 may be provided with a main body 30 including a case or shell 27 with a header 40 having one or more electrical connectors for connecting to leads 60. The generator 10 may be implanted in the patient's chest in a pocket or cavity formed by the implanting surgeon below the skin (indicated by dotted line 90), similar to the implantation procedure for a pacemaker pulse generator. A stimulating nerve electrode assembly 70, such as one including an electrode pair 72, 74, may be conductively connected to the distal end of an insulated electrically conductive lead assembly 60, which may include a pair of lead wires (one wire for each electrode of an electrode set). Each lead wire in lead assembly 60 may be attached at its proximal end to a connector 50 on case 27. The electrode assembly 70 may be surgically coupled to a vagus nerve 100 at a target location, such as the patient's neck, as shown in FIG. 1, above the diaphragm, below the diaphragm, or at a branch of the vagus nerve that innervates the vocal cords, e.g., one or more of a recurrent laryngeal nerve, the external branch of a superior laryngeal nerve, the internal branch of a superior laryngeal nerve, and a pharyngeal plexus.

The electrode assembly 70 may include a bipolar stimulating electrode pair, such as the electrode pair described in U.S. Pat. No. 4,573,481 to Bullara, Mar. 4, 1986. The skilled artisan having the benefit of the present disclosure may appreciate that many electrode designs may be used in the present invention. The electrodes preferably directly contact the vagus nerve 100. As shown in FIG. 1, in a particular embodiment, a spiral electrode may be wrapped about the vagus nerve 100, and the electrode assembly 70 may be secured to the vagus nerve 100 by a spiral anchoring tether, such as that disclosed in U.S. Pat. No. 4,979,511 to Terry, Jr., Dec. 25, 1990 and assigned to the same assignee as the present application. Lead assembly 60 may be secured while retaining the ability to flex with movement of the chest and neck by a suture connection to nearby tissue. While the electrodes 72, 74 of the electrode assembly 70 are shown in FIG. 1 directly contacting the vagus nerve 100, the skilled artisan having the benefit of the present disclosure may appreciate that embodiments in which the electrodes do not directly contact the nerve but are electrically coupled to it are possible.

Electrode assembly 70 may conform to the shape of the nerve, providing a low stimulation threshold by allowing a large stimulation contact area with the nerve. In one embodiment, the electrode assembly 70 may include two electrode ribbons (not shown), formed of a conductive material such as platinum, iridium, platinum-iridium alloys, or oxides of the foregoing. The electrode ribbons may be individually bonded to an inside surface of an elastomeric body portion of the spiral electrodes 72, 74. Although spiral electrodes suitable for direct coupling to a main branch of the vagus nerve have been described, other electrodes, e.g., paddle electrodes, may be more suitable for coupling to branches of the vagus nerve that may present challenging surgical fields.

Lead assembly 60 may include two distinct lead wires or a coaxial cable with two conductive elements respectively coupled to one of the conductive electrode ribbons 72, 74. One suitable method of coupling the lead wires or cable to the electrodes includes a spacer assembly such as that disclosed in U.S. Pat. No. 5,531,778, although other coupling techniques may be used. The elastomeric body portion of each loop may be formed of silicone rubber. Although FIG. 1 illustrates a system for stimulating the left vagus nerve in the neck (cervical) area, the skilled artisan having the benefit of the present disclosure will understand the stimulation signal may be applied to the right cervical vagus nerve in addition to or instead of the left vagus nerve, and all such embodiments are within the scope of the present invention. In such embodiments, lead and electrode assemblies substantially as discussed above may be coupled to the same or a different generator. FIG. 1 also illustrates an external programming system capable of wireless (e.g., radio frequency, RF) communication with the signal generator 10, which may be used to program a therapeutic electrical signal in the signal generator. The external programming system may include a wand 170 having an RF transmitter and receiver, and a computer 160, which may include a handheld computer operable by a healthcare practitioner. Wand 170 may communicate with a receiver and transmitter in signal generator 10, and may be used to receive date from or transmit data to the signal generator 10. Other communications systems, such as communication systems without a wand and operating in the MICS band at 402-405 MHz, may also be used.

Figure 2B:
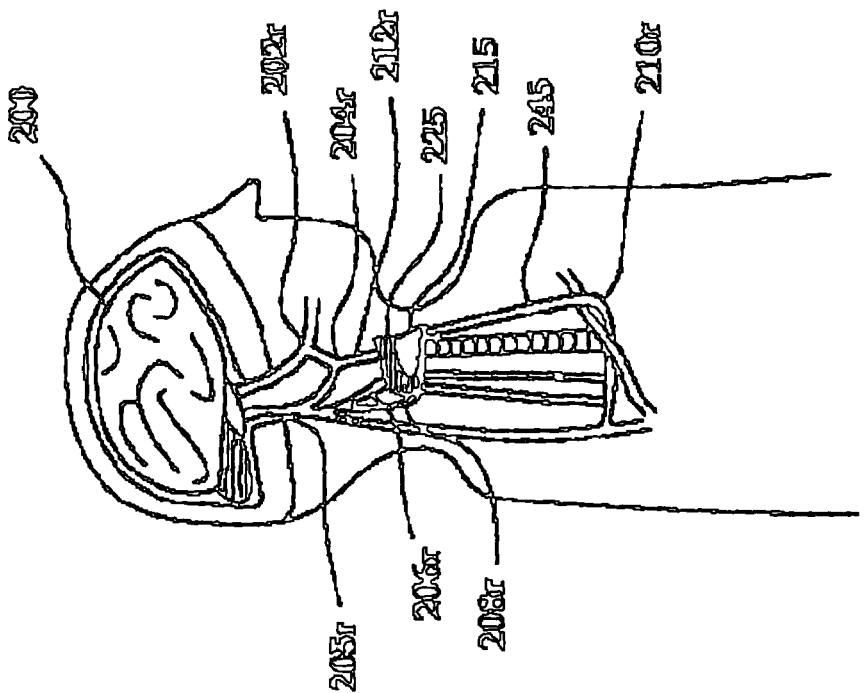
FIG. 2B is a schematic right view of the same sagittal cross-section, in accordance with one embodiment of the present invention.
Figure 2A:
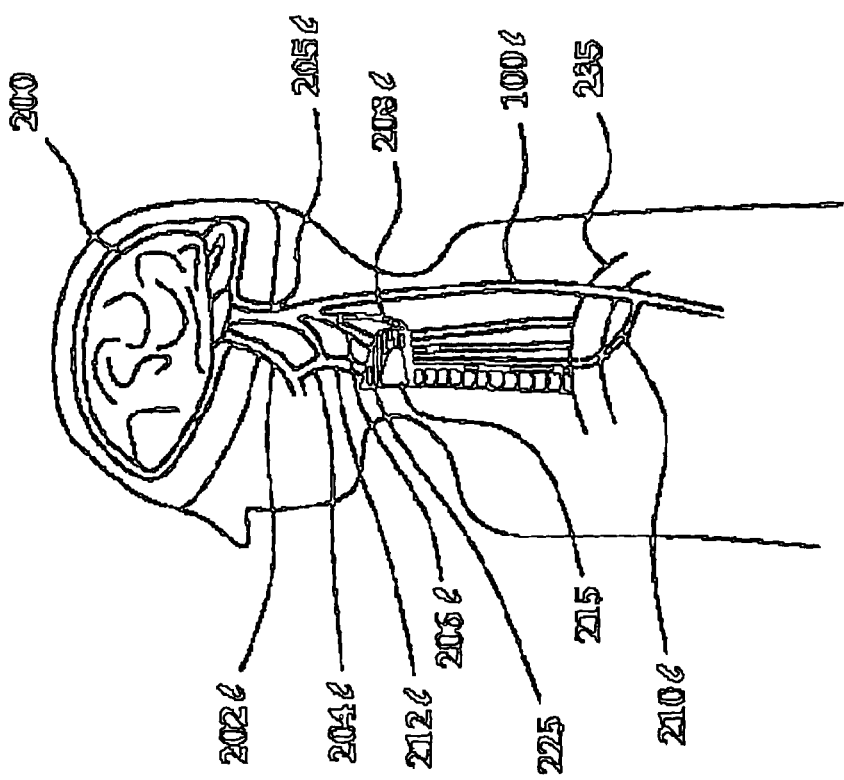
FIG. 2A is a schematic left view of a sagittal cross-section of the head, neck, and upper chest of a person with attention to the left glossopharyngeal nerve, the left vagus nerve, and plexi and branches thereof, in accordance with one embodiment of the present invention.

FIG. 2A is a schematic left view of a sagittal cross-section of the head, neck, and upper torso of a person with attention to the left glossopharyngeal nerve, the left vagus nerve, and plexi and branches thereof. The left vagus nerve 100*l* and the left glossopharyngeal nerve 202*l* emerge from the brain 200 and exit the skull at the left jugular foramen 205*l*. Branches of the nerves 100*l*, 202*l* meet to form the pharyngeal plexus 204*l*. The external branch 206*l* of the left superior laryngeal nerve, the internal branch 208*l* of the left superior laryngeal nerve, the left recurrent laryngeal nerve 210*l*, and branch 212*l* of the pharyngeal plexus innervate the musculature 225 in the vicinity of the larynx 215.

FIG. 2B is a schematic right view of the same sagittal cross-section, with like structures on the right side of the body indicated with the same reference numerals suffixed with the letter r instead of the letter l. The most notable morphological difference between the two sides is that the left recurrent laryngeal nerve 210*l* branches from the main trunk of the left vagus nerve 100*l* below the aorta 235, whereas the right recurrent laryngeal nerve 210*r* branches from the main trunk of the right vagus nerve 100*r* below the subclavian artery 245.

Figure 3:
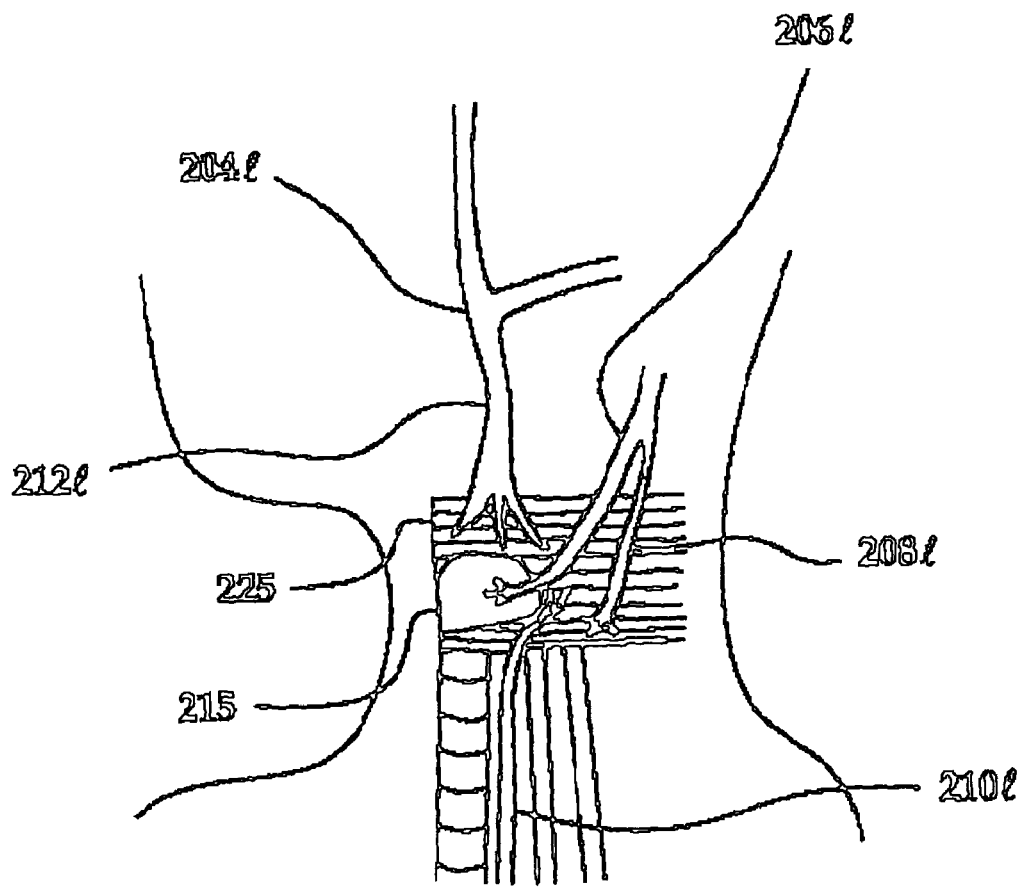
FIG. 3 is a close-up of the larynx and nearby structures shown in FIG. 2A, in accordance with one embodiment of the present invention.

FIG. 3 is a close-up of the larynx 215 and nearby structures shown in FIG. 2A, specifically, the external branch 206*l* of the left superior laryngeal nerve, the internal branch 208*l* of the left superior laryngeal nerve, the left recurrent laryngeal nerve 210*l*, and branch 212*l* of the pharyngeal plexus 204*l* innervate the musculature 225 in the vicinity of the larynx 215.

Figure 4:
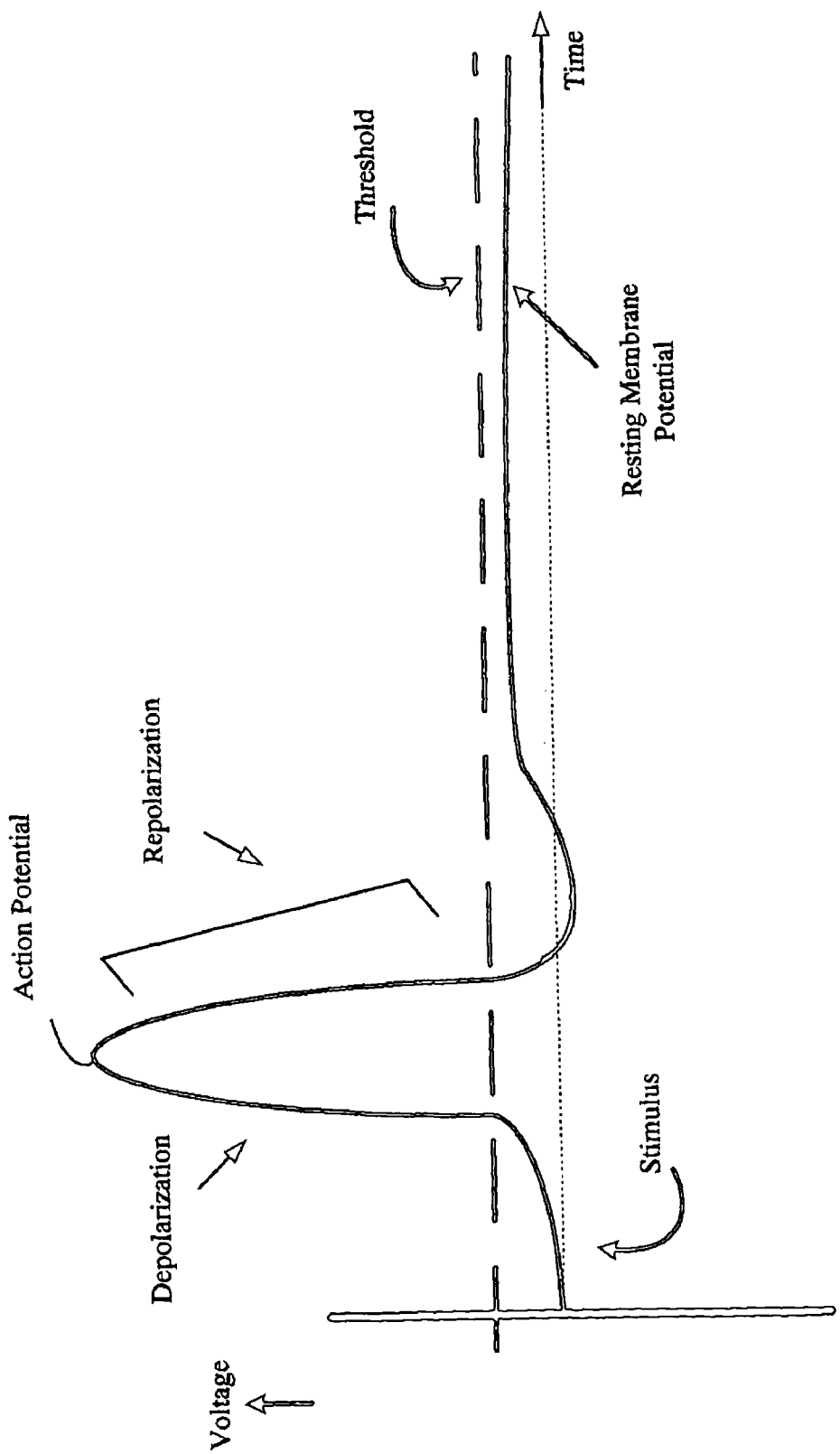
FIG. 4 shows an exemplary electrical signal of a firing neuron as a graph of voltage at a given location at particular times during firing, in accordance with one embodiment of the present invention.

FIG. 4 shows an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). A depolarization interval is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

A cranial nerve may include afferent fibers, efferent fibers, or both. Afferent fibers transmit information to the brain from the extremities; efferent fibers transmit information from the brain to the extremities. The vagus nerve includes both afferent and efferent fibers, and a neurostimulator may be used to stimulate both types of fibers.

A cranial nerve may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa, but this is a general observation, not a rule seen in all cases.

Returning to FIG. 1, neurostimulator 10 may generate electrical signals according to one or more programmed parameters for stimulation of the vagus nerve 100. In one embodiment, the stimulation parameters may be selected from the group consisting of a current magnitude, a pulse frequency, a pulse width, an on-time, and an off-time. A table of ranges for each of these stimulation parameters is provided in Table 1. The stimulation parameter may be of any suitable waveform known in the art of neurostimulation; e.g., a square wave. Various electrical signal patterns may be employed by the neurostimulator. These electrical signals may include a plurality of types of pulses, e.g., pulses with varying amplitudes, polarity, frequency, etc. Other types of signals may also be used, such as sinusoidal waveforms, etc. The electrical signal may be controlled current signals.

TABLE 1

| Parameter | Range |
|---|---|
| Output current | 0-6.0 mA |
| Pulse width | 1 μsec-1 sec |
| Frequency | 0.5-250 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals is generated for stimulating the nerve during the on-time (such a sequence may be referred to as a "pulse burst"), followed by a period in which no signals are generated and the nerve is allowed to recover from the stimulation during the pulse burst. The on/off duty cycle of these alternating periods of stimulation and no stimulation may have a ratio in which the off-time may be set to zero, providing continuous stimulation, or it may be as long as one day or more, in which case the stimulation is provided once per day or at even longer intervals. Typically, however, the ratio off-time/on-time may range from about 0.5 to about 10.

Nominally, the width of each signal may be set to a value not greater than about 1 msec, such as about 250-500 μsec, and the signal repetition frequency may be programmed to be in a range of about 20-250 Hz. A nonuniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

In one embodiment, the present invention may include coupling of at least one electrode to each of two or more cranial nerves. (In this context, two or more cranial nerves means two or more nerves having different names or numerical designations, and does not refer to e.g. the left and right versions of a particular nerve). In one embodiment, at least one electrode may be coupled to each of the vagus nerve and the glossopharyngeal nerve or branches thereof. Each of the nerves in this embodiment or others involving two or more cranial nerves may be stimulated according to particular activation modalities that may be independent between the two nerves.

Another activation modality for stimulation is to program the output of the neurostimulator to the maximum amplitude which the patient may tolerate, with cycling on and off for a predetermined period of time followed by a relatively long interval without stimulation. Where the cranial nerve stimulation system is completely external to the patient's body, higher current amplitudes may be needed to overcome the attenuation resulting from the absence of direct contact with the vagus nerve and the additional impedance of the skin of the patient. Although external systems typically require greater power consumption than implantable ones, they have an advantage in that their batteries may be replaced without surgery.

External stimulation may be used as a screening test to determine if the patient should receive an implanted cranial nerve stimulation system. In one embodiment, the invention includes stimulating the trigeminal nerve, the glossopharyngeal nerve, and/or the vagus nerve with a skin-mounted electrode to determine if the patient is responsive to cranial nerve stimulation for treating the vocal cord disorder. A lead may connect the skin electrode to an electrical pulse generator carried by the patient, e.g., in a pocket or mounted on a belt. The patient may be subjected to relatively high stimulation for a first test period to determine whether the patient's vocal cord disorder is amenable to treatment with cranial nerve stimulation. The symptoms of the patient may be analyzed following the first test period, and a decision may be made whether or not implantation of an implantable system is desirable. If the vocal cord disorder shows a response to the stimulation, the patient may be considered for an implanted system providing direct coupling to a cranial nerve. In certain embodiments, both external stimulation and internal stimulation may be employed to treat the vocal cord disorder.

Other types of indirect stimulation may be performed in certain embodiments of the invention. In one embodiment, the invention includes providing noninvasive transcranial magnetic stimulation (TMS) to the brain of the patient to treat the vocal cord disorder. TMS systems include those disclosed in U.S. Pats. Nos. 5,769,778; 6,132,361; and 6,425,852. Where TMS is used, it may be used in conjunction with cranial nerve stimulation as an adjunctive therapy. In some embodiments, TMS alone may be used to treat the vocal cord disorder. In one embodiment, both TMS and direct cranial nerve stimulation may be performed to treat the vocal cord disorder.

Returning to systems for providing direct cranial nerve stimulation, such as that shown in FIG. 1, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually triggered stimulation, in which the patient manually causes the activation of a pulse burst outside of the programmed on-time/off-time cycle. For example, if the patient undergoes an acute episode of the vocal cord disorder, he may manually activate the neurostimulator to stimulate the cranial nerve to treat the acute episode. The patient may also be permitted to alter the intensity of the signals applied to the cranial nerve within limits established by the physician. For example, the patient may be permitted to alter the signal frequency, current, duty cycle, or a combination thereof. In at least some embodiments, the neurostimulator may be programmed to generate the stimulus for a relatively long period of time in response to manual activation.

Patient activation of a neurostimulator may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating a stimulus generator may include a sensor such as piezoelectric element mounted to the inner surface of the generator case and adapted to detect light taps by the patient on the implant site. One or more taps applied in fast sequence to the skin above the location of the stimulus generator in the patient's body may be programmed into the device as a signal for activation of the generator, whereas two taps spaced apart by a slightly longer duration of time may be programmed into the device as a signal for deactivation of the generator, for example. The therapy regimen performed by the implanted device may remain that which has been preprogrammed by means of an external programmer, according to the prescription of the patient's physician in concert with recommended programming techniques provided by the device manufacturer. In this way, the patient may be given limited but convenient control over operation of the device to an extent which may be determined by the program dictated or entered by the attending physician. The patient may also activate the neurostimulator using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a temperature sensor, a blood parameter sensor, a heart parameter sensor, a brain parameter sensor, or a sensor for another body parameter. The sensor may also include a nerve sensor for sensing activity on a nerve, such as a cranial nerve, such as the vagus nerve, the glossopharyngeal nerve, and/or branches of either nerve that innervate the vocal cords. In one embodiment, the sensor may sense a body parameter that corresponds to a symptom of the vocal cord disorder. If the sensor is to be used to detect a symptom of the vocal cord disorder, a signal analysis circuit may be incorporated into the neurostimulator for processing and analyzing signals from the sensor. Upon detection of the symptom of the vocal cord disorder, the processed digital signal may be supplied to a microprocessor in the neurostimulator device to trigger application of the stimulating signal to the cranial nerve. In another embodiment, the detection of a symptom of interest may trigger a stimulation program including different stimulation parameters from a passive stimulation program, such as having a higher current or a higher ratio of on-time to off-time.

Figure 5A:
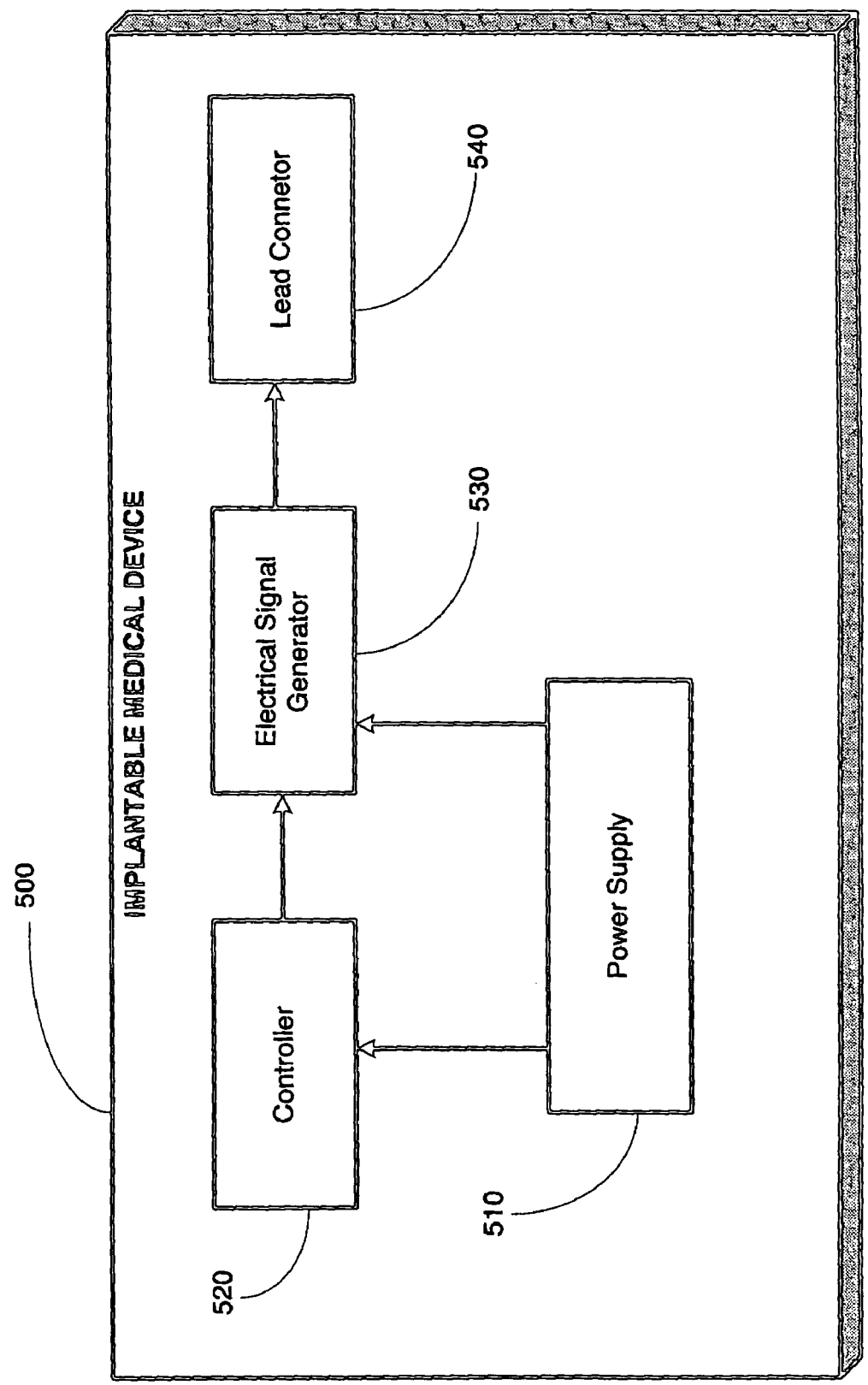
FIGS. 5A-5B show block diagrams of medical devices, in accordance with particular embodiments of the present invention.
Figure 5B:
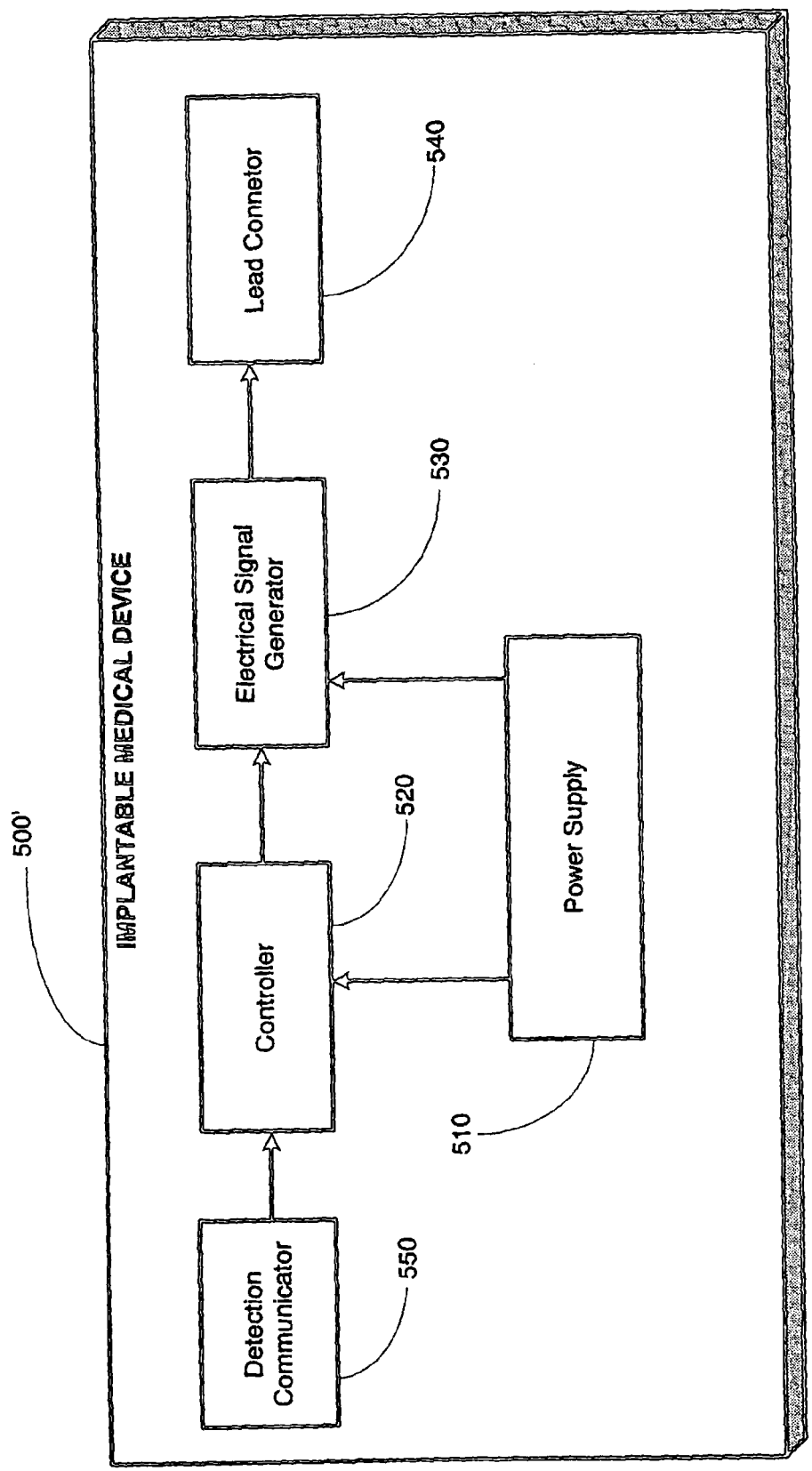

FIG. 5A shows a block diagram of a medical device 500, in accordance with one embodiment of the present invention. The medical device 500 includes a power supply 510 capable of providing power to an operation performed by the medical device; a controller 520 to authorize generation of an electrical signal, and an electrical signal generator 530 to generate an electrical signal upon authorization by the controller and providing the electrical signal to a lead connector 540. FIG. 5B shows a block diagram of an alternative medical device 500' in accordance with one embodiment of the present invention, including the power supply 510, controller 520, electrical signal generator 530, and lead connector 540 referred to above, and further including a further including a detection communicator 550, wherein the power supply 510 is capable of providing power to the detection communicator 550, the detection communicator 550 is capable of delivering at least one signal to the controller 520, and the controller 520 is capable upon receipt of the at least one signal from the detection communicator 550 of authorization of generating an electrical signal by the electrical signal generator 530. In one embodiment, the controller 520 defines stimulation pulses to be delivered to the nerve tissue according to parameters that may be preprogrammed into the device 500. The controller 520, which may include a processor that may execute program code, controls the operation of the electrical signal generator 530, which generates the stimulation pulses according to programmed parameters and provides these pulses to the lead connector 540 for delivery to the patient. The controller 520 may be capable of implementing multi-phasic controlled current signal outputs. The controller 520 may be capable of providing a controlled current signal where pulses may include various amplitudes, varying phases, and varying polarity. The controller 520 may also be capable of providing mono-phasic stimulation signals. The controller 520 may also be capable of switching between various electrodes employed by the device 500.

In an alternative embodiment, based upon various parameters provided to the device 500, the controller 520 may develop a multi-phasic pulse description pattern and provide the same to the electrical signal generator 530 to perform a particular type of multi-phasic stimulation. The controller 520 may be capable of converting stored data relating to the phasic pulse description and may control behavior of the electrical signal generator 530 accordingly. Additionally, the device 500 also may include a burst description array that includes data relating to performing a pulse-to-pulse variation of a stimulation signal. The controller 520 may be capable of using data from the burst description array to provide a stimulation signal that includes a pulse train, where one pulse in the pulse train may vary from another pulse train. This pulse-to-pulse variation may include variations in the pulse width, amplitude, pulse-shape, polarity, etc.

In one embodiment, the medical device 500 or 500' may be implanted into a human body.

Figure 6:
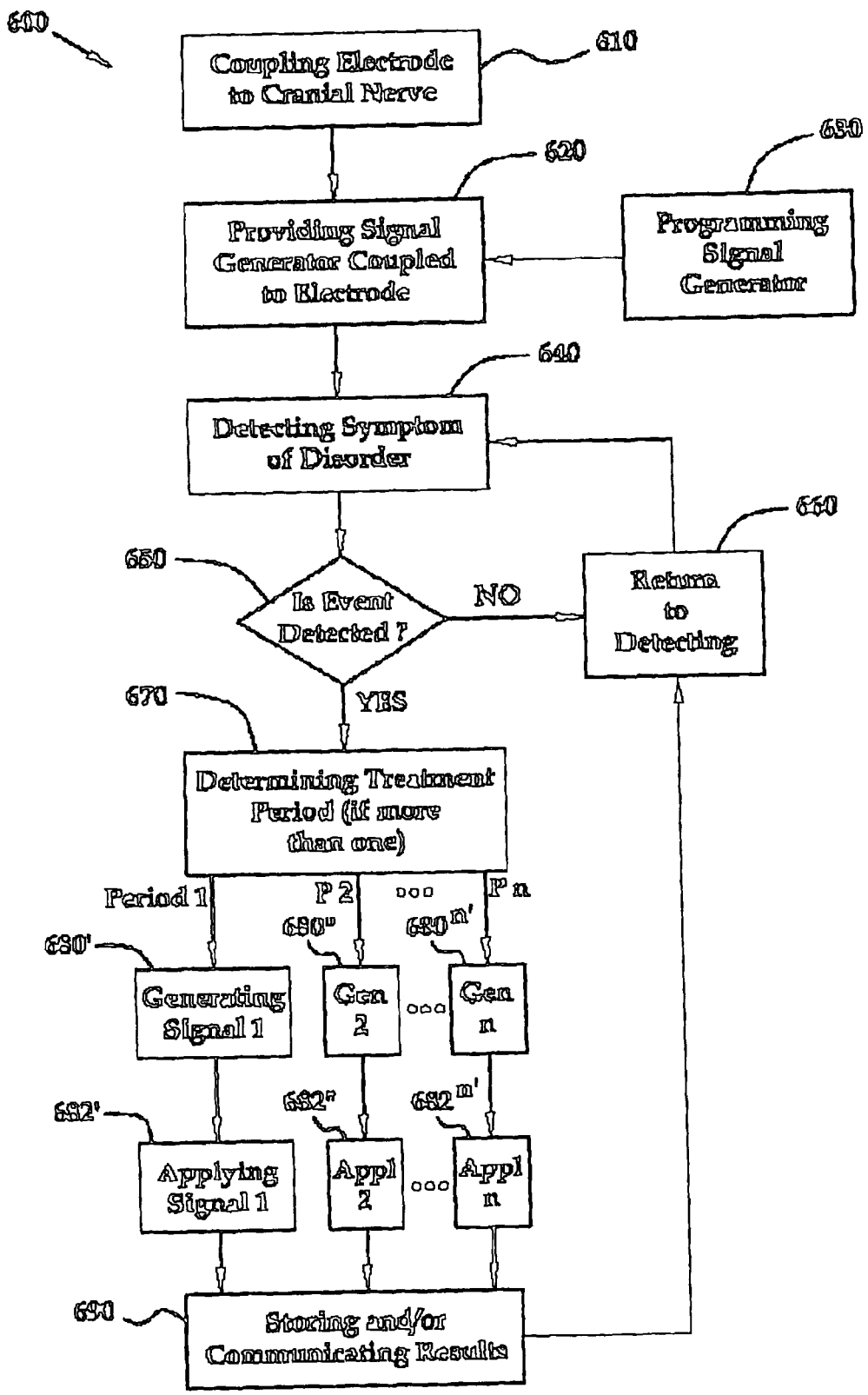
FIG. 6 shows a flowchart of a method of treatment in accordance with one embodiment of the present invention.

FIG. 6 provides a flowchart of the steps of a method 600 in accordance with one embodiment of the present invention. Method 600 includes coupling 610 at least one electrode to at least one cranial nerve of a patient and providing 620 a signal generator coupled to the electrode. The signal generator may programmed in a programming step 630. After the electrode has been coupled 610 and the signal generator has been provided 620, the method 600 may include detecting 640 an event indicative of a symptom of a disorder to be treated. At each execution 650 of the detecting step 640, if an event is not detected, the flow of the method 600 returns 660 to detecting 640. If an event is detected during execution 650, the flow of the method 600 moves to determining 670 the treatment period to implement, if more than one is intended by the healthcare practitioner implementing the method 600. FIG. 6 shows a number n of treatment periods designated prime, double prime . . . , n-prime. Each treatment period includes generating 680', 680'' . . . , 680''' a signal and applying 682', 682'' . . . , 682n' the signal to the electrode coupled 610 to the cranial nerve. After treatment, the results of the treatment may be stored or communicated to other steps in the method 600, such as returning 660 to the detecting step 640.

The method 600 may be performed without a detecting step 640 or detection execution step 650, e.g., may be performed continuously, may be performed according to a preprogrammed schedule, or may be performed after receiving input from the patient, among others.

All of the methods and apparatus disclosed and claimed herein may be made and executed without undue experimentation in light of the present disclosure. While the methods and apparatus of this invention have been described in terms of particular embodiments, it will be apparent to those of skill in the art that variations may be applied to the methods and apparatus and in the steps or in the sequence of steps of the method described herein without departing from the concept, spirit and scope of the invention as defined by the appended claims. It should be especially apparent that the principles of the invention may be applied to selected cranial nerves other than the vagus nerve to achieve particular results.

What is claimed is:

1. A method of treating a patient having a vocal cord disorder selected from the group consisting of vocal cord paralysis and vocal cord trauma, comprising:
coupling at least one electrode to at least one cranial nerve of the patient selected from the group consisting of a vagus nerve, a trigeminal nerve, and a glossopharyngeal nerve;
applying an electrical signal to the at least one cranial nerve using the electrode to treat the vocal cord disorder, and
detecting a symptom of the vocal cord disorder, wherein applying the electrical signal is initiated in response to detecting said symptom.

2. The method of claim 1 wherein the vocal cord disorder comprises vocal cord paralysis.

3. The method of claim 1, wherein coupling at least one electrode to at least one cranial nerve comprises coupling the electrode to a branch of the vagus nerve of the patient selected from the group consisting of a recurrent laryngeal nerve, the external branch of a superior laryngeal nerve, the internal branch of a superior laryngeal nerve, and a pharyngeal plexus.

4. The method of claim 1, further comprising generating a physiological response to said electrical signal that is selected from the group consisting of an afferent action potential, an efferent action potential, an afferent hyperpolarization, and an efferent hyperpolarization.

5. The method of claim 4, wherein applying the electrical signal comprises generating an efferent action potential.

6. The method of claim 1, further comprising the steps of:
providing a programmable electrical signal generator;
coupling said signal generator said at least one electrode;
generating an electrical signal with the electrical signal generator;
and applying the electrical signal to the electrode.

7. The method of claim 6, further comprising programming the electrical signal generator to define the electrical signal by at least one parameter selected from the group consisting of a current magnitude, a pulse frequency, a pulse width, an on-time and an off-time, wherein said at least one parameter is selected to treat the vocal cord disorder.

8. The method of claim 1, wherein the detecting the symptom comprises using a voice sensor.

9. The method of claim 1, wherein applying the electrical signal comprises applying said signal during a first treatment period, and said method further comprises applying a second electrical signal to the cranial nerve using the at least one electrode during a second treatment period to treat the vocal cord disorder.

10. The method of claim 1, wherein detecting the symptom comprises using a voice sensor.

11. A method of treating a patient having a vocal cord disorder selected from the group consisting of vocal cord paralysis and vocal cord trauma, comprising:
coupling at least one electrode to at least one cranial nerve of the patient selected from the group consisting of a vagus nerve, a trigeminal nerve, and a glossopharyngeal nerve;
providing an electrical signal generator;
coupling said signal generator to said at least one electrode;
generating an electrical signal with the electrical signal generator;
applying the electrical signal to the electrode to treat the vocal cord disorder, and
detecting a symptom of the vocal cord disorder, wherein applying the electrical signal is initiated in response to detecting said symptom.

12. The method of claim 11 wherein coupling at least one electrode to at least one cranial nerve comprises coupling at least one electrode to a branch of the vagus nerve of the patient selected from the group consisting of a recurrent laryngeal nerve, the external branch of a superior laryngeal nerve, the internal branch of a superior laryngeal nerve, and a pharyngeal plexus.

13. A method of treating a patient having a vocal cord disorder selected from the group consisting of vocal cord paralysis and vocal cord trauma, comprising:
coupling at least one electrode to at least one branch of a vagus nerve of the patient selected from the group consisting of a recurrent laryngeal nerve, the external branch of a superior laryngeal nerve, the internal branch of a superior laryngeal nerve, and a pharyngeal plexus;
applying an electrical signal to said at least one branch of a vagus nerve using the electrode to treat the vocal cord disorder, and
detecting a symptom of the vocal cord disorder, wherein applying the electrical signal is initiated in response to detecting said symptom.

14. The method of claim 13 further comprising:
providing a programmable electrical signal generator;
coupling said signal generator to said at least one electrode;
generating an electrical signal with said electrical signal generator; and
wherein applying an electrical signal to said at least one branch of a vagus nerve comprises applying the electrical signal to said at least one electrode.

15. The method of claim 14, further comprising:
programming the electrical signal generator to define said electrical signal by a plurality of parameters selected from the group consisting of a current magnitude, a pulse width, a pulse frequency, an on-time and an off-time.

16. The method of claim 13, wherein applying an electrical signal to said at least one branch of a vagus nerve comprises applying said signal during a first treatment period, said method further comprising applying a second electrical signal to the at least one branch of a vagus nerve during a second treatment period.

17. The method of claim 16, wherein said first treatment period comprises a period ranging from one hour to six months, and wherein said second treatment period comprises a period ranging from one month to 10 years.

18. The method of claim 13, wherein the at least one electrode is selected from the group consisting of a spiral electrode and a paddle electrode.

* * * * *